US00PP12305P2

(12) United States Plant Patent
Tobutt

(10) Patent No.: US PP12,305 P2
(45) Date of Patent: Dec. 25, 2001

(54) SAMBUCUS PLANT NAMED 'GERDA'

(75) Inventor: Kenneth Richard Tobutt, Meopham (GB)

(73) Assignee: Horticulture Research International, East Malling (GB)

( * ) Notice: Subject to any disclaimer, the term of this patent is extended or adjusted under 35 U.S.C. 154(b) by 0 days.

(21) Appl. No.: 09/425,231

(22) Filed: Oct. 21, 1999

(51) Int. Cl.[7] ..... A01H 5/00
(52) U.S. Cl. ..... Plt./226
(58) Field of Search ..... Plt./226

(56) References Cited

PUBLICATIONS

UPOV–ROM GTITM Computer Database 20000/05, GTI JOUVE Retrieval Software, citation(s) for 'GERDA' Oct. 10, 2000.*

* cited by examiner

*Primary Examiner*—Bruce R. Campell
*Assistant Examiner*—Annette Para

(57) ABSTRACT

A new cultivar of *Sambucus nigra* named 'Gerda' that is particularly distinguished in having dark purple foliage and flowers that have deep purple-pink petal markings and deep purple-pink anthers, styles and pedicels.

2 Drawing Sheets

BACKGROUND OF THE INVENTION

This new invention presents a new cultivar of Elderberry, *Sambucus nigra*, herein referred to as 'Gerda'. 'Gerda' is unique in that it has very dark purple-red foliage and an intense pink flower coloration. The pink coloration of 'Gerda' is defined by the pink lower surface of the petals, the pink tips on the petals, and the deep pink color of the anthers, styles and pedicels.

'Gerda' was selected from a seedling population. The first generation cross was made in 1990 between *Sambucus nigra* 'Pyramidalis' (unpatented) and *Sambucus nigra* 'Guincho Purple' (unpatented). 'Pyramidalis' (aka 'Fastigiata') has a more erect habit, the foliage is green, and the flowers are a creamy white. 'Guincho Purple' is similar in habit to 'Gerda', however the foliage color is lighter, more bronze and often flecked with green and the flowers are creamy white with pale pink anthers, styles and pedicels. A subsequent cross was made between two selected seedlings from the original cross in June of 1993. Approximately 100 flowers were hand-pollinated and then bagged for protection until a seed harvest that resulted in 203 seedlings being planted out for evaluation in 1994. The new variety 'Gerda' was selected from these seedlings in 1996 on the basis of its purple-pink flowers and intense purple-red, almost black foliage. In addition to comparisons made to the parents, the foliage color is also much darker in comparison to the cultivar 'Thundercloud' (unpatented). All crosses and selections were done in West Malling, Kent in England.

The new invention was first propagated by softwood cuttings from the mother plant by the inventor in West Malling in 1996 and found to be true to type in successive generations.

SUMMARY OF THE INVENTION

The following characteristics have been repeatedly observed and represent the attributes of the new cultivar. These characteristics in combination distinguish this cultivar from its parents and others cultivars currently available in commerce.

1. The foliage of 'Gerda' is a very dark purple-red with purple veins and purple stems. It is darker than 'Guincho Purple' (unpatented) and 'Thundercloud' (unpatented).
2. The flowers of 'Gerda' have more pink coloration than 'Guincho Purple'. The lower surface of the petals and the tips of the petals are purple-pink and the anthers, styles, and pedicels are a deep pink color. The flowers of 'Guincho Purple' are creamy white with pale pink anthers, styles and pedicels.

BRIEF DESCRIPTION OF THE DRAWINGS

Sheet One contains a photo of a two year old example of *Sambucus nigra* 'Gerda' as grown in the landscape in West Malling, Kent England.

On Sheet Two, the upper photo is a close-up of the fully open flowers and the lower photo is of a vase containing cuttings of foliage, flowers and berries. The color is as accurate as possible by conventional photography.

BOTANICAL DESCRIPTION OF THE PLANT

The following is a detailed description of the new cultivar as grown outdoors in East Malling, Kent, England. Phenotypic differences may be observed with variations in environmental, climatic, and cultural conditions. The color determination is in accordance with the R.H.S. Colour Chart of The Royal Horticultural Society, London, England, except where general color terms of ordinary dictionary significance are used.

Botanical classification: 'Gerda' is a cultivar of *Sambucus nigra*. Caprifoliaceae family.

Commercial classification: Elderberry, 'Gerda' is sold under the name 'Black Beauty'.

Parentage: $F_2$ generation *Sambucus nigra* 'Pyramidalis' and *Sambucus nigra* 'Gunicho Purple'.

Plant description:

*Blooming period.*—May to July in the UK with flowers lasting two to three weeks.

*Plant habit*.—Upright, dense shrub, slightly spreading, vigorous.

*Height and spread*.—3 m in height and spread if left un-pruned.

*Hardiness*.—Has been found to tolerate UK climatic conditions with temperatures typically in the range −5° C. to +30° C. Zone 4–9.

*Type*.—Deciduous shrub.

*Root system*.—Fibrous.

*Propagation*.—Nodal or inter-nodal softwood cuttings inserted into coarse free draining compost with bottom heat (~20° C.) and top heat (~18° C.), keeping the leaves wet (95–100% humidity) with fine mist, shaded from direct light, day length set at 16 hours. Roots typically appear after 14 days, rooted and ready to wean after 28 days, fully weaned after 40 days.

*Culture*.—Sunny to part-shade location, moist but well-drained, moderately fertile soils. Can be pruned to control vigor and shape.

*Diseases and pests*.—No known unique susceptibility or resistance.

Stems: Young stems are green to purple (144A–79A). Shoots 1 to 2 years old are gray with a slight green sheen and are smooth except for large gray lenticels (~2 mm in diameter, ~8 per square inch); solid white pith. Older branches have rough furrowed gray-brown (199C) bark. The stem color is purple (187A).

Leaves:

*Shape*.—Ovate to elliptic.

*Division*.—Pinnate (usually 5 leaflets).

*Margins*.—Serrulate. Surface. Glossy, metallic.

*Size*.—Leaflets are 8–12 cm long and 4–6 cm wide.

*Color*.—Leaf buds are 187A. The young foliage appears pale green with a hint of purple. The mature foliage is dark purple (202A) on the upper surface and a pale purple (187A–202B) on the lower surface. Occasional paler, greener flecks (147B) can be seen on the leaves. Veins are 187A on the upper side and 59A on the lower side. Autumn foliage color is 200B–166A. Upper and lower surfaces are glabrous except for sparse hairs along veins.

Flowers:

*Infloresence type*.—Flat polychasium, umbel-like cyme~20 cm diameter, individual flower~3 mm from ovary base to anther tip.

*Size*.—6–7 mm (diameter of corolla).

*Flower structure*.—5 orbicular petals, ~2 mm across, alternating with the 5 anthers, sepals minimal, style disk-like and very short~1 mm. Stigma: Minimal, <1 mm diameter. Pollen: Pale yellow color (~4D).

*Flower color*.—Buds are 72A,. Upper and lower surfaces of petals are purple red (72A) at tips fading to off-white (155D) at base. Anthers, pedicels and style arms are 53D–60C.

Fruit:

*Color*.—Very dark purple-black surface (187A–202) (red flesh).

*Shape*.—Globosa.

*Presence*.—August–September.

*Size*.—6 mm in diameter.

Seeds: Approximately three straw colored seeds~2 mm×3 mm per drupe.

I claim:

1. A new and distinct cultivar of *Sambucus nigra* named 'Gerda' as described and illustrated.

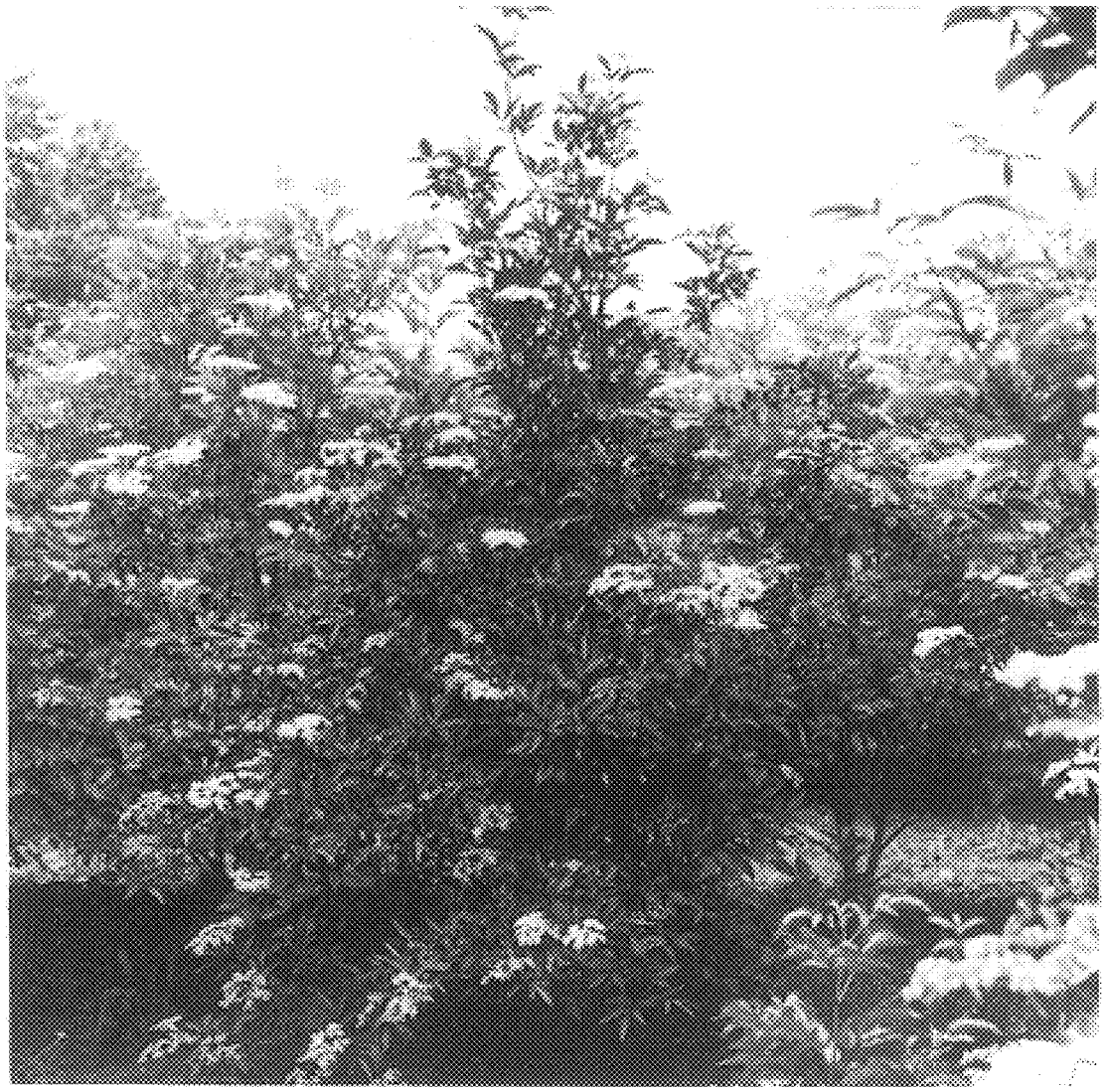

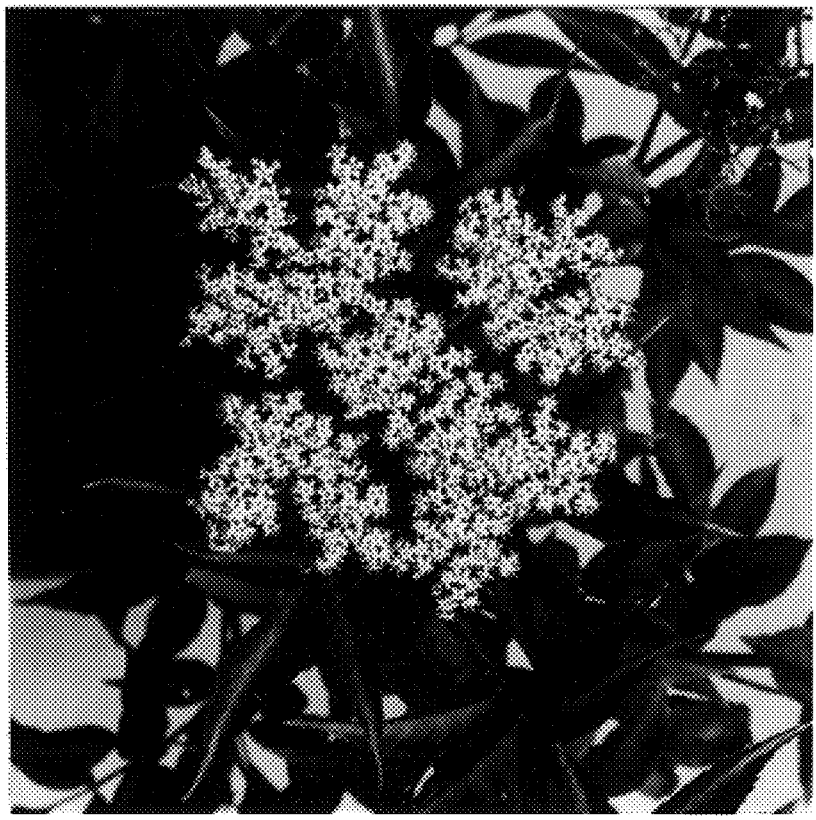
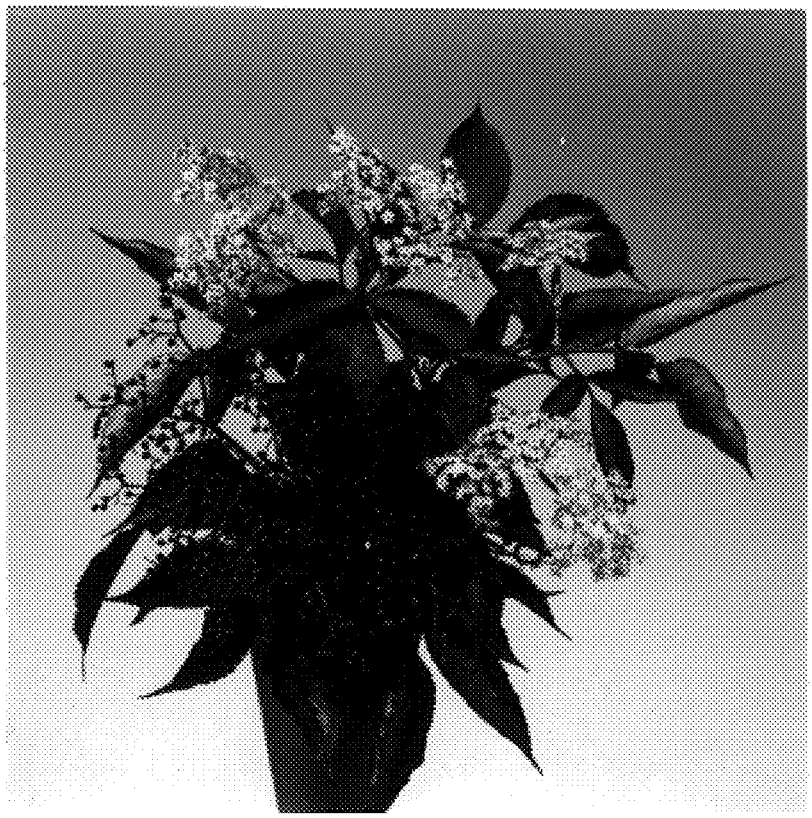

* * * * *